(12) United States Patent
Wang et al.

(10) Patent No.: US 9,376,410 B2
(45) Date of Patent: Jun. 28, 2016

(54) (2R)-2-DEOXY-2,2-DISUBSTITUTED-RIBONO-1,4-LACTONE AND PREPARATION METHOD AND USE THEREOF

(71) Applicants: TOPHARMAN SHANGHAI CO., LTD., Pudong, Shanghai (CN); SHANGHAI INSTITUTE OF MATERIA MEDICA, CHINESE ACADEMY OF SCIENCES, Pudong, Shanghai (CN); TOPHARMAN SHANDONG CO., LTD., Weifang, Shandong (CN)

(72) Inventors: Guan Wang, Shanghai (CN); Xiangrui Jiang, Shanghai (CN); Xudong Gong, Shanghai (CN); Weiming Chen, Shandong (CN); Fuqiang Zhu, Shanghai (CN); Rongxia Zhang, Shanghai (CN); Xianguo Zhao, Shanghai (CN)

(73) Assignees: TOPHARMAN SHANGHAI CO., LTD., Shanghai (CN); SHANGHAI INSTITUTE OF MATERIA MEDICA, CHINESE ACADEMY OF SCIENCES, Shanghai (CN); TOPHARMAN SHANDONG CO., LTD., Shandong (CN)

(*) Notice: Subject to any disclaimer, the term of this patent is extended or adjusted under 35 U.S.C. 154(b) by 0 days.

(21) Appl. No.: 14/434,563

(22) PCT Filed: Oct. 10, 2013

(86) PCT No.: PCT/CN2013/084967
§ 371 (c)(1),
(2) Date: Apr. 9, 2015

(87) PCT Pub. No.: WO2014/056442
PCT Pub. Date: Apr. 17, 2014

(65) Prior Publication Data
US 2015/0284351 A1 Oct. 8, 2015

(30) Foreign Application Priority Data

Oct. 10, 2012 (CN) .......................... 2012 1 0383012

(51) Int. Cl.
C07D 307/00 (2006.01)
C07D 307/33 (2006.01)
C07D 413/12 (2006.01)

(52) U.S. Cl.
CPC ............ *C07D 307/33* (2013.01); *C07D 413/12* (2013.01)

(58) Field of Classification Search
CPC ..................................................... C07D 307/33
USPC ....................................................... 549/319
See application file for complete search history.

(56) References Cited

U.S. PATENT DOCUMENTS

| 8,669,382 B2 | 3/2014 | Ishii et al. |
| 8,912,321 B2 | 12/2014 | Axt et al. |
| 2008/0145901 A1 | 6/2008 | Cedilote et al. |

FOREIGN PATENT DOCUMENTS

| CN | 101 573 349 | 11/2009 |
| CN | 101 591 371 | 12/2009 |
| CN | 101 600 725 | 12/2009 |
| CN | 101469010 | * 11/2011 ................. 549/319 |
| WO | WO 2006/119347 | 11/2006 |
| WO | WO 2007/075876 | 7/2007 |
| WO | WO 2008/045419 | 4/2008 |
| WO | WO 2008/090046 | 7/2008 |
| WO | WO 2011/152155 | 12/2011 |
| WO | WO 2012/142093 | 10/2012 |
| WO | WO 2013/177219 | 11/2013 |

OTHER PUBLICATIONS

Dorwald F. A. Side Reactions in Organic Synthesis, 2005, Wiley: VCH, Weinheim p. IX of Preface p. 1-15.*
Arya et al. Tetrahedraon 2000, 56, 917-947.*
Elsner et al. Chem. Commun., 2008, 5827-5829.*
Zhang et al. Tetrahedron: Asymmetry, 20, 2009, 305-312.*

(Continued)

*Primary Examiner* — Nizal Chandrakumar
(74) *Attorney, Agent, or Firm* — Jenkins, Wilson, Taylor & Hunt, P.A.

(57) ABSTRACT

This invention disclose (2R)-2-deoxy-2,2-disubstituted-ribono-1,4-lactone in a single configuration and preparation method and use thereof. The (2R)-2-deoxy-2,2-disubstituted-ribono-1,4-lactone, or a pharmaceutically acceptable salt, an ester, a prodrug or a solvate thereof according to the invention are important intermediates of a variety of anti-viral and anti-tumor active ingredients. A compound obtained from (2R)-2-deoxy-2,2-disubstituted-ribono-1,4-lactone via an acylation reaction can be directly used for preparing various anti-viral and anti-tumor drugs. The Chiral synthesis method and the spontaneous resolution method of the compound of (2R)-2-deoxy-2,2-disubstituted-ribono-1,4-lactone according to the invention have the following advantages: the reaction routes are short and simple with high yield and low cost, which are suitable for industrial application.

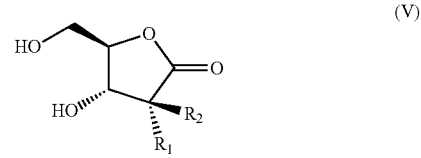

(V)

4 Claims, No Drawings

(56) References Cited

OTHER PUBLICATIONS

Brunet, V.A. et al., "Titanium mediated asymmetric aldol reaction with α-fluoropropionimide enolates," Journal of Fluorine Chemistry, 2007, vol. 128, pp. 1271-1279, see Schemes 6, 4.1.6 and 4.1.7, p. 1272

Wang, Peiyuan et al. "An efficient and diastereoselective synthesis of PSI-6130: A clinically efficacious inhibitor of HCV NS5B polymerase," Journal of Organic Chemistry, 2009, vol. 74, pp. 6819-6824.

Zhang, Pingsheng et al., "A practice synthesis of (2R)-3,5-di-O-benzoyl1-2-fluoro-2-C-methyl-D-ribono-γ-lactone," Tetrahedron: Asymmetry, 2009, vol. 20, pp. 305-312, see compounds 9 and 28, p. 309, Scheme 6, and p. 310, section 4.2.

International Search Report for Application No. PCT/CN2013/084967 dated Jan. 16, 2014.

* cited by examiner

(2R)-2-DEOXY-2,2-DISUBSTITUTED-RIBONO-1,4-LACTONE AND PREPARATION METHOD AND USE THEREOF

FIELD OF INVENTION

This invention relates to the field of medicinal chemistry and chemical synthesis, in particular, relates to (2R)-2-deoxy-2,2-disubstituted-ribono-1,4-lactone in a single configuration and preparation method and use thereof.

BACKGROUND ART 2-deoxy-2,2-disubstituted-ribono-1,4-lactone and derivatives thereof are important intermediates of a variety of anti-viral and anti-tumor active ingredients. For example, these compounds were used as raw materials in the development of anti-hepatitis C drugs PSI-7977 and R7128 with the following structures by Pharmasset Company. The two anti-hepatitis C drugs are currently undergoing clinical experiments.

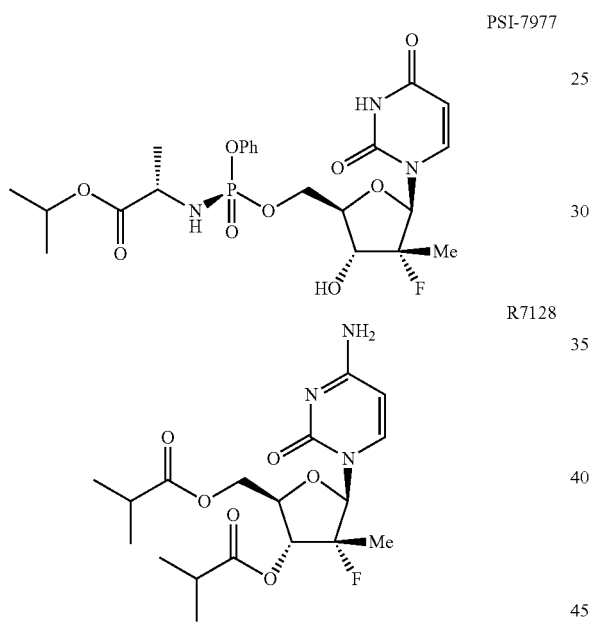

The routes for preparing the 2-deoxy-2,2-disubstituted-ribono-1,4-lactone and derivatives thereof have been reported. For example, a preparation method as shown in Scheme 1 was reported in WO2008045419 and J. Org. Chem, 2009, 74, 6819-6824, in which the asymmetric synthesis method is applied to control the chirality of C-2 position, however the disadvantages thereof is longer route, relatively complicated operation and low yield. Further, in the preparation method as shown in Scheme 1, it is not easy to control the quality of the intermediates resulting in the unstable quality of the final product, because some of the intermediates are unstable.

Scheme 1:

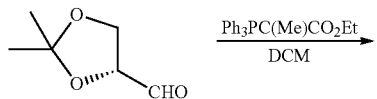

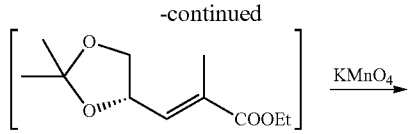

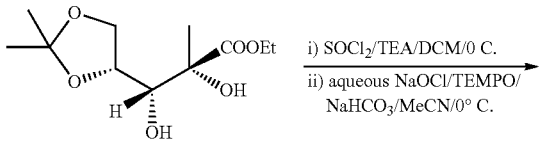

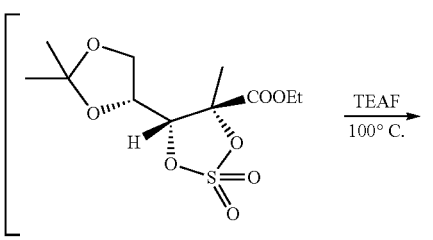

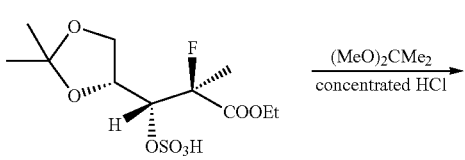

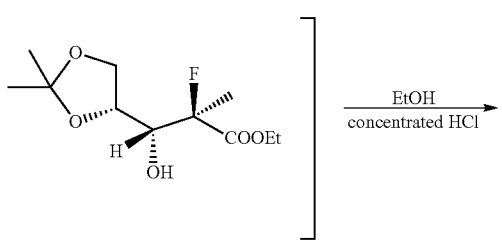

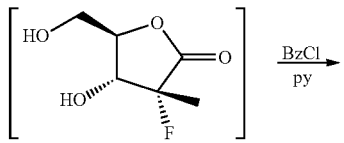

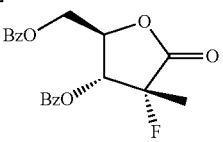

A preparation method as shown in Scheme 2 was reported in US20080145901 and Tetrahedron: Asymmetry, 2009, 20, 305-312.

Scheme 2:

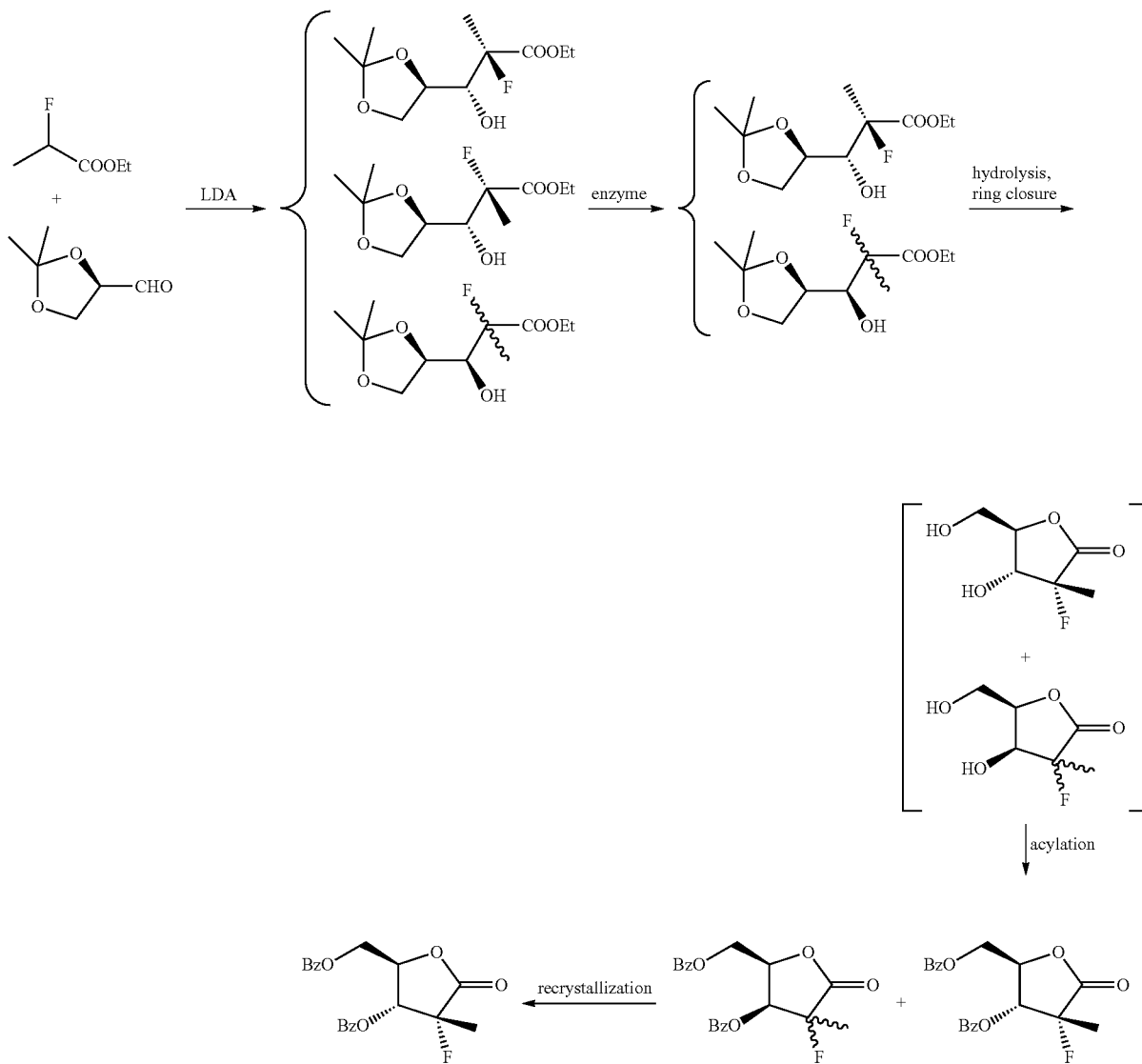

In the chemical reaction according to the above method, the two steps of selective enzymatic hydrolysis and crystallization are carried out without controlling the chirality of C-2 position, so as to achieve the purpose of resolution. However, this approach requires a large amount of buffer or the like, has relatively low preparation efficiency, and is not suitable for large-scale application. in addition, since the first step of reaction requires low temperature reaction condition, in which strong base such as lithium diisopropylamide (LDA) and so on has to be used and the harsh reaction conditions are required, it has relatively high demand on the equipment.

A preparation method as shown in Scheme 3 was reported in WO2008090046, in which the title compound was synthesized by replacing ethoxy in US20080145901 with non-chiral auxiliary group having a large steric hindrance (for example, pyrrole, thiophenol, or benzoxazolone) to form large sterically hindered amide or thiophenol ester. However, in this method, the chiral selectivity is not high, and the maximal the de value of the obtained product is only 56%.

Scheme 3:

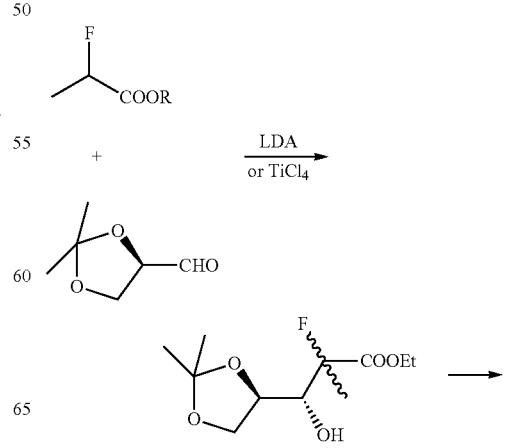

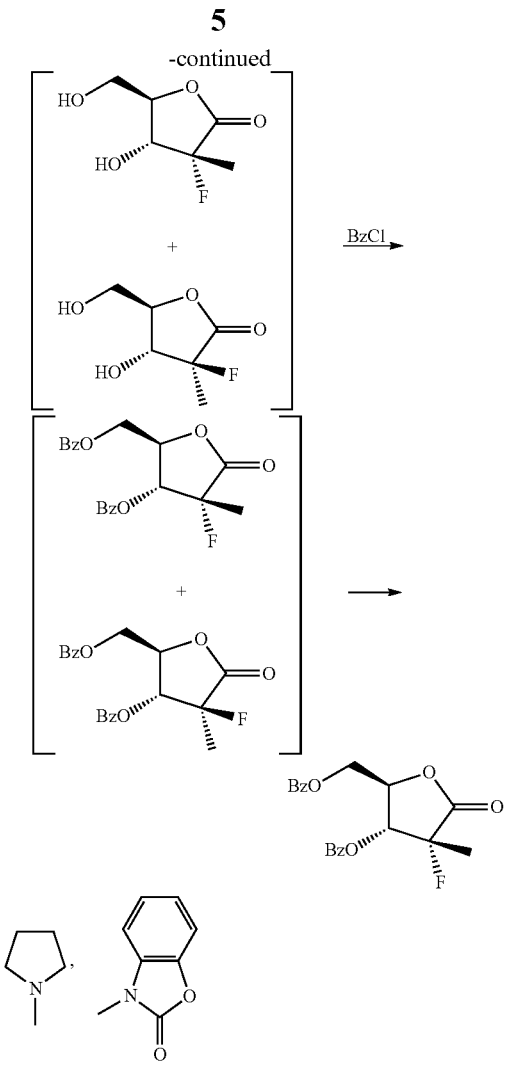

R = SPh, [pyrrolidine], [methyl benzoxazolone]

Therefore, it is still need to find out a method for preparing the (2R)-2-deoxy-2,2-disubstituted-ribono-1,4-lactone with high steric selectivity, high yield and low cost, and suitable for industrial application.

DISCLOSURE OF INVENTION

Technical Object

In order to solve the deficiencies in the prior art, an object of the present invention is to provide (2R)-2-deox:$_y$r-2,2-disubstituted-ribono-L4-lactone in a single configuration, or pharmaceutically salt, an ester, a prodrug or a solvate thereof, which is an important intermediate of a variety of anti-viral and anti-tumor active ingredients.

Another object of the present invention is to provide a method for chirally synthesizi rig (2R)-2-deoxy-2,2-disubstituted-ribono-1,4-lactone in a single configuration by using the chiral auxiliary group.

A further object of the present invention is to provide a method for separating (2R)-2-deoxy-2,2-disubstituted-ribono-1,4-lactone in a single configuration from a mixture of stereoisomers by using a crystallization method.

Still another object of the present invention is to provide a use of (2R)-2-deoxy-2,2-disubstituted-ribono-1,4-lactone in a single configuration.

Technical Solution

To achieve the above objects, the present invention provides (2R)-2-deoxy-2,2-disubstituted-ribono-1,4-lactone represented by the following General Formula V, or a pharmaceutically acceptable salt, an ester, a prodrug or a solvate thereof:

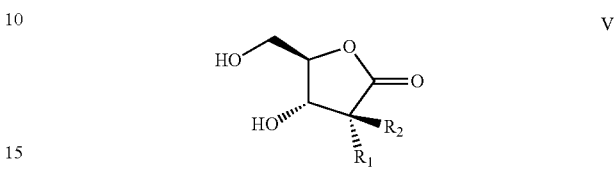

wherein $R_1$ and $R_2$ are different and are each independently selected from the group consisting of hydrogen, halogen, nitrite group, carbamoyl group and $C_1$-$C_3$ linear or branched alkyl group, wherein the halogen is fluorine, chlorine, bromine or iodine, Preferably, $R_1$ and $R_2$ are each independently selected from the group consisting of $C_1$-$C_3$ linear or branched alkyl group and halogen.

Another technical solution according to the present invention is to provide a method for chirally synthesizing (2R)-2-deoxy-2,2-disubstituted-ribono-1,44actone in a single configuration by using the chiral auxiliary group, which is carried out by the following reaction Formula:

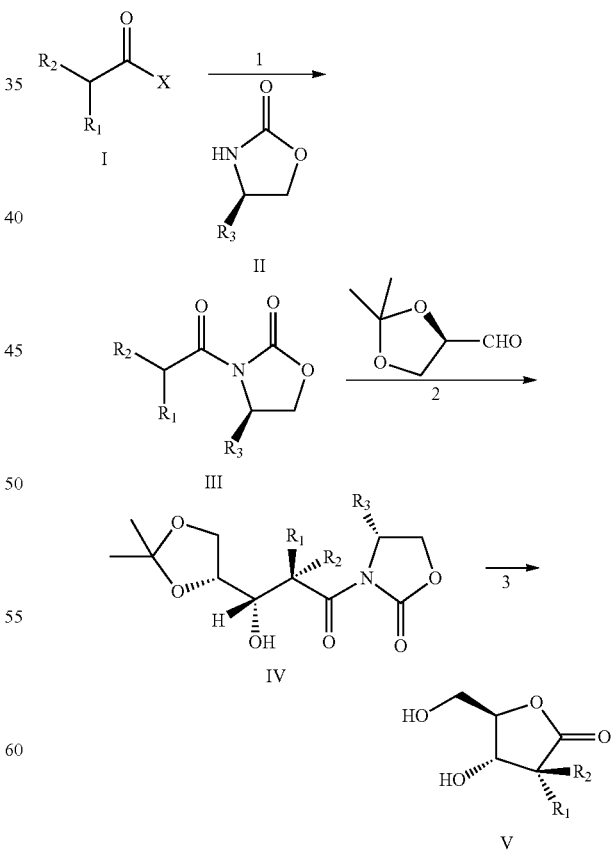

wherein $R_1$ and $R_2$ are as same as defined in General Formula V; $R_3$ is phenyl or t-butyl; and X is hydroxyl or halogen, wherein a compound represented by Formula I is a substituted acetic acid or substituted acetyl halide, and a compound represented by Formula II is 4-substituted oxazolone, the method comprises the following steps:

1) performing a condensation reaction between the compound represented by Formula I and the compound represented by the Formula II in the presence of a condensing agent to obtain a compound represented by Formula III, in the case that X is hydroxyl (i.e., the compound represented by Formula I is the substituted acetic acid), or performing an acylation reaction between the compound represented by Formula I and the compound represented by the Formula II in the presence of an acid binding agent to obtain the compound represented by Formula III, in the case that X is halogen (i.e., the compound represented by Formula I is the substituted acetyl halide);

2) performing an Aldo condensation reaction between the compound represented by Formula III and (R)-(+)-2,2-dimethyl-1,3-dioxolane-4-carboxaldelyde(D-glyceraldehyde acetonide) in the presence of a Lewis acid and an organic base to obtain a compound represented by Formula IV, which may be used in the next reaction step without further purification;

3) performing a deprotection reaction (i.e. removing isopropylidene, substituted oxazolone) and ring closure of the compound represented by Formula IV in an acidic system to obtain a compound represented by General Formula V.

4) after performing the steps of 2) and 3) in one-pot reaction to obtain compound of Formula IV, removing the Lewis acid by forming a complex, a salt or a double salt.

In the above method, the condensing agent used in Step 1) is selected from the group consisting of dicyclohexyl carbodiimide (DCC) and 1-ethyl-(3-dimethylaminopropypcarbodiimide; the acid binding agent used in Step 1) is an organic or inorganic base, and may be selected from the group consisting of potassium carbonate, sodium carbonate, triethylamine, pyridine, N,N-dimethyl-4-aminopyridine, diisopropyiethylaraine and imidazole; the solvent used in Step 1) is a non-protic solvent, and may be selected from the group consisting of dichloromethane (DCM), 1,2-dichloroethane, tetrahydrofuran, 1,4-dioxane, toluene, acetonitrile, ethyl acetate and ethylene glycol dimethyl ether; the reaction temperature of Step 1) may be changed within a wide range, typically −20° C.~100° C., preferably −20° C.~40° C. In addition, the substituted acetic acid may also be converted to the substituted acetyl halide in the presence of a halogenating agent (e.g. thionyl chloride, oxalyl chloride, etc.).

In the above method, the Lewis acid used in Step 2) is selected from the group consisting of titanium tetrachloride, tin tetrachloride, fenic chloride and zinc chloride, preferably titanium tetrachloride; the organic base used in Step 2) is selected from the group consisting of triethylamine, diisopropylethylamine, 1,8-diazabicyclo[5.4.0]undec-7-ene (DBU), pyridine and N,N-dimethyl-4-aminopyridine; the solvent used in Step 2) is a non-protic solvent, and may be selected from the group consisting of dichloromethane, 1,2-dichloroethane, tetrahydrofuran, 1,4-dioxane, toluene, acetonitrile, ethyl acetate and ethylene glycol ditnethyl ether; the reaction temperature of Step 2) may be changed within a wide range, typically −20° C.~100° C., preferably −10° C.~60° C.

In the above method, the acidic system in Step 3) is a mixture of a protonic acid, such as hydrochloric acid, sulfuric acid, acetic acid or trifluoroacetic acid, and alcoholic solvent (e.g. methanol, ethanol, propanol or isopropanol); the reaction temperature of Step 3) may be changed within a wide range, typically 20° C.~100° C., preferably 40° C.~100° C.

In the above method, the complex or salt in Step 4) comprises insoluble organic complexes, inorganic complexes, organic salts, inorganic salts or double salt.

A further aspect of the present invention is to provide a method for separating (2l)-2-deoxy-2,2-disubstituted-ribono-1,4-lactone in a single configuration from a mixture of stereoisomers by using a crystallization method, which can be carried out by the following reaction Formula:

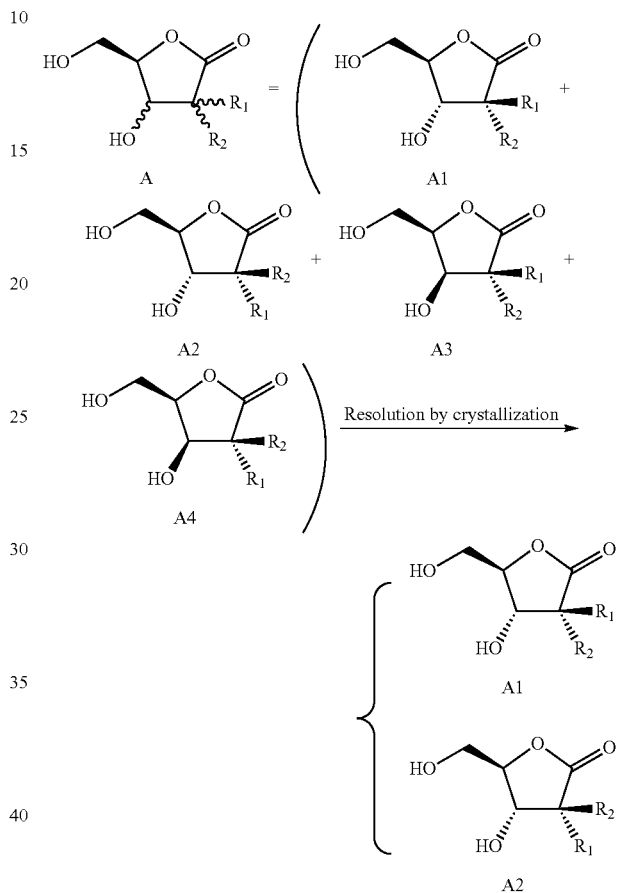

wherein $R_1$ and $R_2$ are as same as defined in General Formula V, the compound represented by General Formula A2 (Compound A2) is the compound represented by General Formula V.

the method comprises the following steps:

1) adding solvent V1 to Compound A, dissolving Compound A preferably at temperature of −20~80° C., and performing the following processes:

① constantly maintaining or reducing the temperature of the above-mentioned solution in which Compound A is dissolved, to precipitate the solid; or ② volatilizing a part of solvent V1 of the solution in which Compound A is dissolved, to precipitate the solid; or ③ adding another solvent V2 to the above-mentioned solution in which Compound A is dissolved, to precipitate the solid, wherein the solvent V2 is different from the solvent V1;

and then filtering to obtain the solid, which is one of Compounds A1 and A2; and 2) drying the mother liquor in Step 1) by concentration, and repeating the operation of Step 1), to obtain another one of Compounds A1 and A2.

The above Compound A is a mixture of Compounds A1, A2, A3 and A4 with different configurations, the molar content of each configuration compound is greater than zero, the molar ratio of each configuration compound is (A1+A2)>(A3+A4), and the molar content of Compounds A1 and A2 is A1:A2>1.1, or A2:A1>1.1

In the above aspect, if the resultant solid obtained in Step 1 or 2) is impure, the operation of Step 1) or 2) can be repeated to improve the purity.

Further, the method of the present invention may be carried out for Compound A, that is, Compounds A1 and A2 can be crystallized and seperated from the mixture of four stereoisomers—compound A. Or the method may be carried out for the mixture of Compounds A1 and A2, namely dissolving Compound A in solvent V1, then precipitating and filtering the solid to obtain the solid mixture of Compounds A1 and A2, and then Compounds A1 and A2 can be seperated by performing the operation of Step 1) or 2) again.

In the above technical solution, the solvents V1 and V2 may be each independently selected from the group consisting of water; hydrocarbons such as benzene, xylene, toluene, methylene chloride or chloroform; ethers such as tetrahydrofuran, ethyl ether, propyl ether, or 1,4-dioxane; amides such as N,N-dimethylformamide, N,N-diethylformamide or N,N-dimethylacetamide; esters such as ethyl acetate; ketones such as acetone; alcohols such as methanol, ethanol, propanol or isopropanol; acids such as acetic acid; nitriles such as acetonitrile; and any combination thereof. The solvent V1 is preferably selected from the group consisting of toluene, methylene chloride, ethyl acetate, acetonitrile, acetone, tetrahydrofuran, ethanol, and any combination thereof. The solvent V2 is preferably selected from the group consisting of dichloromethane, petroleum ether, toluene, tetrahydrofuran, ethyl acetate, acetone, n-hexane, methanol, ethanol, isopropanol, 1,4-dioxane, and any combination thereof.

In the above technical solution, the weight ratio of the solvent V1 to Compound A is 0.005 to 200, preferably 0.1 to 15. The weight ratio of the solvent V1 to the solvent V2 is 0.05 to 500, preferably 0.2 to 50.

In the above technical solution, $R_1$ and $R_2$ are each independently selected from the group consisting of $C_1$-$C_3$ linear or branched alkyl group and halogen, and when $R_1$ is methyl and $R_2$ is fluorine or chlorine, the technical solution of the present invention may preferably be as follows:

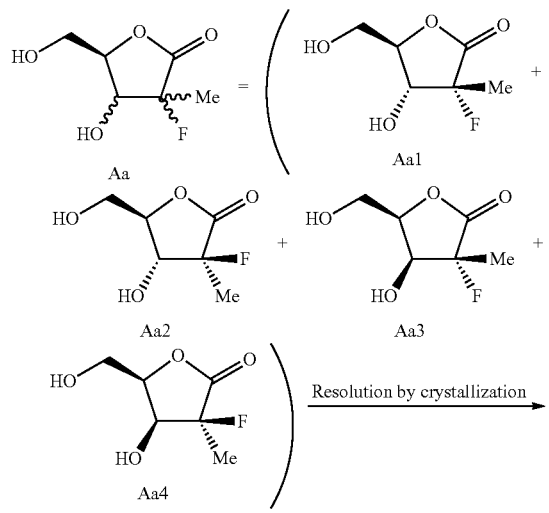

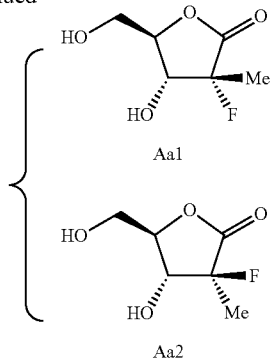

It was reported in Tetrahedron: Asymmetry, 2009, 20, 305-312 that the molar ratios of the stereoisomers of prepared Compound Aa is Aa:Aa1:Aa2:(Aa3+Aa4)=51:38:11. However, the present method (i.e., Resolution by crystallization) can effectively provide pure Compounds Aa1 and Aa2 in a single configuration (confirmed by $^1$H-NMR detection). Through a benzoylating process, The resulting Compound Aa2 can be transferred to (2R)-3,5-dibenzoyl-2-fluoro-2-C-methyl-D-ribonolactone with purity of above 99%.

A further aspect of the present invention provides a use of (2R)-2-deoxy-2,2disubstituted-ribono-1,4-lactone represented by Formula V, wherein (2R)-2-deoxy-2,2-disubstituted-ribono-1,4-lactone represented by Formula V is subjected to an acylation process in the presence of an acid binding agent to give a compound represented by Formula VI,

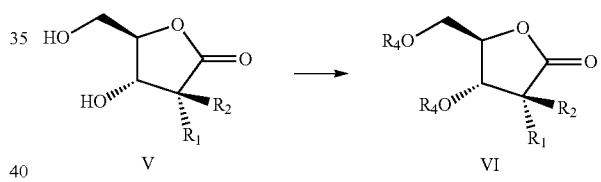

wherein $R_1$ and $R_2$ are as same as defined in General Formula V; $R_4$ can be any group, preferably trimethylsilyl group; t-butyldimethylsilyl group; an unsubstituted or substituted $C_6$-$C_{12}$ arolyl group; cinnamoyl; or $C_1$-$C_6$ linear or branched acyl, or 6-9 membered ring protecting group formed by two $R_4$.

In the above method, the acid binding agent used is an organic or inorganic base, and may be selected from the group consisting of potassium carbonate, sodium carbonate, triethylamine, pyridine, N,N-dimethyl-4-aminopyridine, diisopropylethylamine and imidazole; the solvent used is aprotic solvent, and may be selected from the group consisting of dichloromethane, 1,2-dichloroethane, tetrahydrofuran, 1,4-dioxane, toluene, acetonitrile, ethyl acetate and ethylene glycol dimethyl ether; and the temperature of the acylation reaction may be in the wide range, typically 0° C.~100° C., preferably 20° C.~60° C.

Beneficial Effects

The present invention provides (2R)-2-deoxy-2,2-disubstituted-ribono-1,4-lactone represented by the following General Formula V, or a pharmaceutically acceptable salt, an ester, a prodrug or a solvate thereof, which is an important intermediate of a variety of anti-viral and anti-tumor active ingredients. In addition, the compound represented by General Formula VI obtained from the compound represented by General Formula V through an acylation reaction can be directly used for preparing various anti-viral and anti-tumor drugs.

The present invention provides a method for chirally synthesizing (2R)-2-deoxy-2,2-disubstituted-ribono-1,4-lactone in a single configuration by using the chiral auxiliary group, in which the stereoselectivity may be controlled during the growing of the chiral center in light of the steric hindrance effect of the chiral auxiliary group, and the chiral auxiliary group used can be recovered. Therefore, this method has advantages of high stereoselectivity, high yield, low cost, mild reaction conditions, and so on.

Meanwhile, the method according to the present invention for separating (2R)-2-deoxy-2,2-disubstituted-ribono-1,4-lactone in a single configuration from a mixture of stereoisomers by using the crystallization method, can separate Compound A (i.e. 2-deoxy-2,2-disubstituted-ribono-1,4-lactone) by using Resolution by crystallization on the base of the difference in solubility of stereoisomers in solvent, and further to obtain stereoisomers A1 and A2 in a single configuration. Therefore, this method has the following advantages: the short and simple reaction process, high yield, low cost, suitability for industrial application.

BEST MODE

The embodiments of the present invention will be described by providing the following examples. However, it should be appreciated that the embodiments of the present invention are not limited to the specific details of the following examples, since it is known and obvious for an ordinary skilled person in the art to make other variations, in view of the present disclosure.

EXAMPLE 1

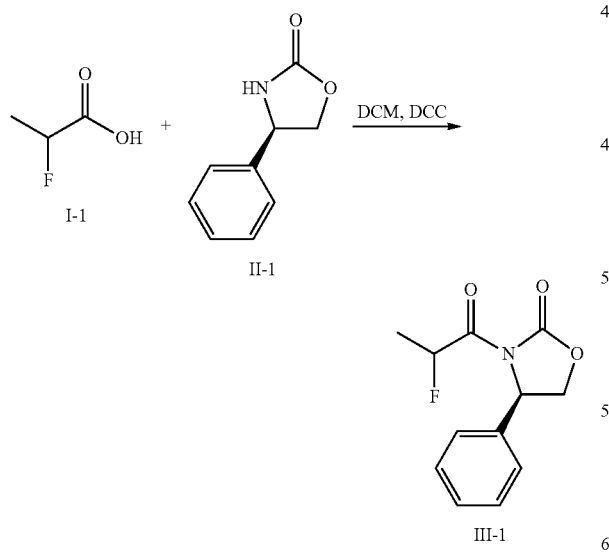

R-4-phenyl-2-oxazolidone (4g, 24.5 mmol) was dissolved in 50 mL of dichloromethane, and then dicyclohexyl carbodiimide (1.5 eq) and 2-fluoro-propionic acid (1.3 eq) were respectively added therein. After the raw materials were completely reacted indicating by TLC, filtering the solid, drying the organic phase by concentration, then 2 mL of methanol was added. The resulting mixture was stirred for 3 h and filtered to give 4.3 g white solid in a yield of 73.9%.

EXAMPLE 2

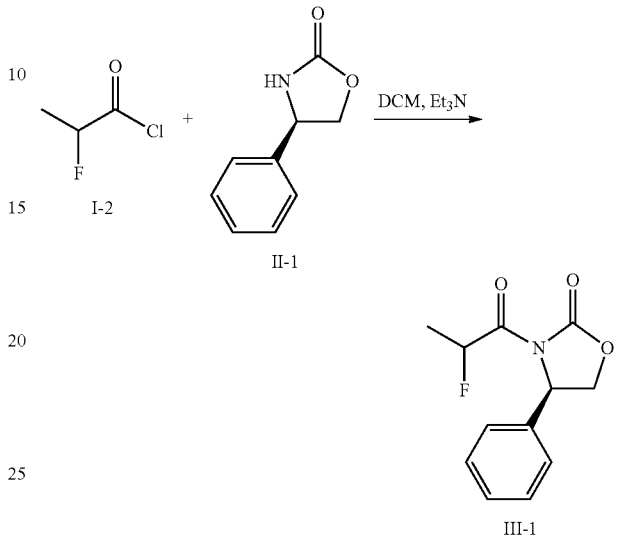

R-4-phenyl-2-oxazolidone (4 g, 24.5 mmol) was dissolved in 50 mL of dichloromethane, and then triethylamine (5.2 mL, 1.5 eq) was added therein. Subsequently, 2-fluoro-propionyl chloride (1.3 eq) was slowly added dropwise at 0° C.~5° C. After the raw materials were completely reacted indicating by TLC, filtering the solid, drying the organic phase by concentration, then 20 mL of methanol was added. The resulting mixture was stirred for 3 h and filtered to give 5 g white solid in a yield of 86.0%.

EXAMPLE 3

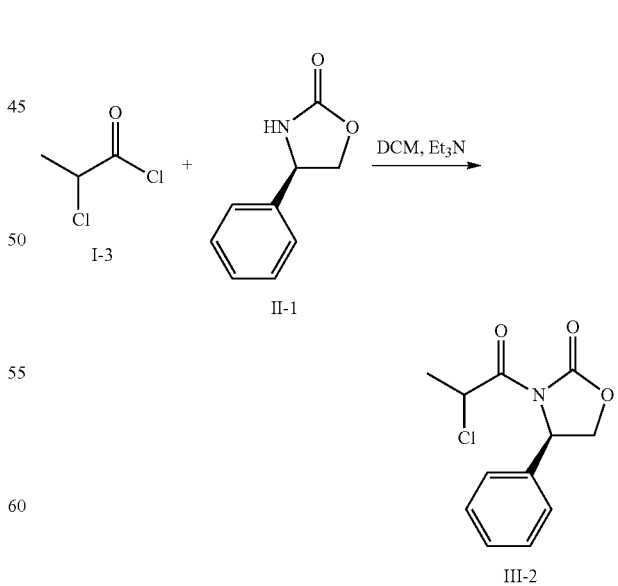

R-4-phenyl-2-oxazolidone (4 g, 24.5 mmol) was dissolved in 50 mL of dichloromethane, and then triethylamine (5.2 mL, 1.5 eq) was added therein. Subsequently, 2-chloro-propionyl chloride (1.3 eq) was slowly added dropwise at 0° C.~5° C. After the raw materials were completely reacted indicating by TLC, filtering the solid, drying the organic phase by concentration, then 20 mL of methanol was added. The resulting mixture was stirred for 3 h and filtered to give 4.5 g white solid in a yield of 72.5%.

EXAMPLE 4

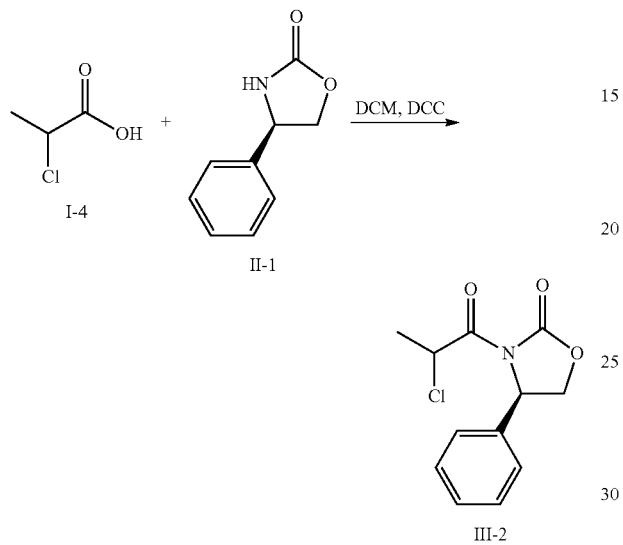

R-4-phenyl-2-oxazolidone (4 g, 24.5 mmol) was dissolved in 50 mL of dichloromethane, and then dicyclohexyl carbodiimide (1.5 eq) and 2-chloro-propionic acid (1.3 eq) were respectively added therein. After the raw materials were completely reacted indicating by TLC, tittering the solid, drying the organic phase by concentration, then 20 mL of methanol was added. The resulting mixture was stirred for 3 h and filtered to give 4.3 g white solid in a yield of 69.3%.

EXAMPLE 5

R-4-phenyl-2-oxazolidone (4 g, 24.5 mmol) was dissolved in 50 mL of dichloromethane, and then triethylamine (5.2 mL, 1.5 eq) was added therein. Subsequently, 2-methyl-butyryl chloride (1.3 eq) was slowly added dropwise at 0° C. ~5° C. After the raw materials were completely reacted indicating by TLC, filtering the solid, drying the organic phase by concentration, then 20 mL of methanol was added. The resulting mixture was stirred for 3 h and filtered to give 4.3 g white solid in a yield of 72.5%.

EXAMPLE 6

R-4-phenyl-2-oxazolidone (4 g, 24.5 mmol) was dissolved in 50 mL of dichloromethane, and then dicyclohexyl carbodiimide (1.5 eq) and 2-methyl-butyric acid (1.3 eq) were respectively added therein. After the raw materials were completely reacted indicating by TLC, filtering the solid, drying the organic phase by concentration, then 20 mL of methanol was added. The resulting mixture was stirred for 3 h and filtered to give 4.3 g white solid in a yield of 72.5%.

EXAMPLE 7

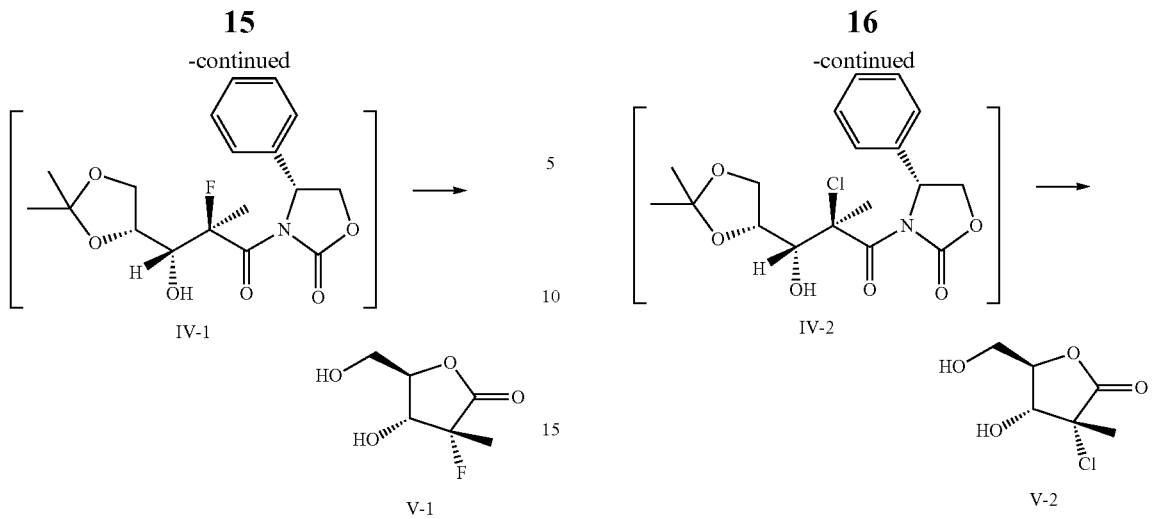

Compound III-1 (8.0 g, 34 mmol) was dissolved in 50 mL of dichloromethane. 10 mL dichloromethane solution containing titanium tetrachloride (6.80 mL, 2 eq) was added dropwise therein at the temperature of −5° C.~0° C. After completion of addition, the resulting mixture was stirred for 1 h. Subsequently, 10 mL dichloromethane solution containing triethylamine (6.6 mL, 1.5 eq) was added dropwise therein at the temperature of −5 ° C.~0 ° C. After completion of addition, the resulting mixture was incubated and stirred for 2.5 h, Subsequently, a dichloromethane solution containing (R)-(+)-2,2-dimethyl-1,3-dioxolane-4-carboxaldehyde (12.26 g, 1.3 eq) was added dropwise therein at the temperature of −5° C.~−15° C. After completion of addition, the resulting mixture was incubated for 2 h. The resulting mixture was stirred at room temperature overnight, and dried under reduced pressure to remove the DCM. 80 mL of ethanol and 5 mL of concentrated hydrochloric acid were added therein. The resulting mixture was refluxed for 4 h, and then the reaction mixture was concentrated to a small volume and 100 mL of water was added. The resulting mixture was beaten and filtered to recover Compound 11-1. The solid was washed with 20 mL of water. The aqueous phase was combined and extracted with methylene chloride/water, then drying the aqueous layer to give a tan oily substance which was purified by silica gel column chromatography to obtain 2.9 g of the solid compound V-1. Yield: 52.0%.

¹HNMR(300 MHz, DMSO-d6):δ 1.46 (d, 3H, J=24 Hz), 3.55 (dd, 1H, J=12.8, 4.4 Hz), 3.73-3.80 (m, 1H), 3.96 (dd, 1H, J=24, 8 Hz), 4.20-4.28 (m, 1H).

EXAMPLE 8

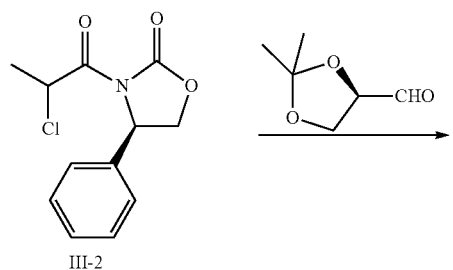

Compound III-2 (8.0 g, 32 mmol) was dissolved in 50 mL of dichloromethane. 10 mL dichloromethane solution containing titanium tetrachloride (6.80 mL, 2 eq) was added dropwise therein at the temperature of −5° C.~0°C. After completion of addition, the resulting mixture was stirred for 1 h. Subsequently, 10 mL dichloromethane solution containing triethylamine (6.6 mL, 1.5 eq) was added dropwise therein at the temperature of −5° C.~0° C. After completion of addition, the resulting mixture was incubated and stirred for 2.5 h. Subsequently, a dichloromethane solution containing (R)-(+)-2,2-dimethyl-1,3-dioxolane-4-carboxaldehyde (12.26 g, 1.3 eq) was added dropwise therein at the temperature of −5° C.~−15° C. After completion of addition, the resulting mixture was incubated for 2 h. The resulting mixture was stirred at room temperature overnight, and dried under reduced pressure to remove the DCM. 80 mL of ethanol and 5 mL of concentrated hydrochloric acid were added therein. The resulting mixture was refluxed for 4 h, and then the reaction mixture was concentrated to a small volume and 100 mL of water was added. The resulting mixture was beaten and filtered to recover Compound II-1. The solid was washed with 20 mL of water. The aqueous phase was combined and extracted with methylene chloride/water, then drying the aqueous layer to give a tan oily substance which was purified by silica gel column chromatography to obtain 2.7 g of the solid compound V-2. Yield: 46.9%.

¹HNMR(300 MHz, CD3OD):δ=1.70 (s, 3H), 3.72 (dd, 1H), 3.97 (dd, 1H), 4.14 (d, 1H), 4.25 (m, 1H).

Compound III-2 (2.0 g, 7.9 mmol) was dissolved in 15 mL of dichloromethane. dichloromethane solution containing titanium tetrachloride (0.88 mL, 1 eq) was added dropwise thereto at the temperature of −5~0° C. After completion of addition, the resulting mixture was stirred for 1 h. Subsequently, 3 ml dichloromethane solution containing triethytamine (1.7 mL, 1.5 eq) was added dropwise therein at the temperature of −5° C.~0° C. After completion of addition, the resulting mixture was incubated and stirred for 2.5 h. Subsequently, a dichloromethane solution containing (R)-(+)-2,2-dimethyl-1,3-dioxolane-4-carboxaldetyde (3.1 g, 1.3 eq) was added dropwise therein at the temperature of −5° C.~15° C. After completion of addition, the resulting mixture was incubated for 2 h. The resulting mixture was stirred at room temperature overnight, and dried under reduced pressure to remove the DCM. 20 mL of ethanol and 5 mL of concentrated hydrochloric acid were added therein. The resulting mixture was refluxed for 4 h, and then the reaction mixture was concentrated to a small volume and 100 mL, of water was added. The resulting mixture was beat and filtered to recover Compound II-1. The solid was washed with 20 mL of water. The aqueous phase was combined and extracted with methylene chloride/water. To the aqueous layer, oxalic acid (2.7 g, 30 mmol.) was added, then heating in oil bath at 75° C. for 5 minutes, adding 10 mL aqueous solution containing barium chloride (3.67 g, 15 mmol) in one time and precipitating the solid. The resulting mixture was incubated and stirred for 0.5 h, and then cooled to room temperature, filtered, and washing the filter cake twice with acetone. The filtrate was dried and 25 mL of acetone was added to the residue to filter again, and then the filter cake was washed with 10 mL acetone. After drying the filtrate, the residue was dehydrated twice with acetone and toluene to give an acidic yellow oily substance. The oily substance was purified by short silica. gel column chromatography to obtain 0.5 g of the solid Compound V-2. Yield: 35.2%.

EXAMPLE 9

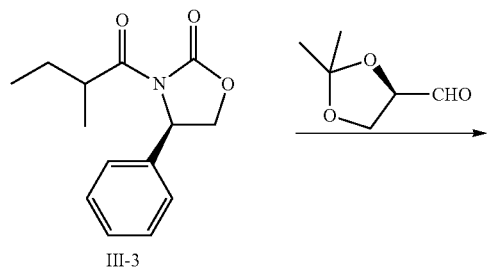

III-3

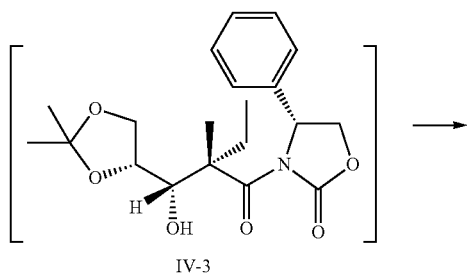

IV-3

Compound III-3 (8.0 g, 32 mmol) was dissolved in 50 mL of dichloromethane, 10 mL dichloromethane solution containing titanium tetrachloride (6.80 mL, 2 eq) was added dropwise therein at the temperature of −5° C.~0° C. After completion of addition, the resulting mixture was stirred for 1 h. Subsequently, 10 mL dichloromethane solution containing triethylamine (6.6 mL, 1.5 eq) was added. dropwise therein at the temperature of −5° C.~0° C. After completion of addition, the resulting mixture was incubated and stirred for 2.5 h. Subsequently, a dichioromethane solution containing (R)-(+)-2,2-dimethyl-1,3-dioxolane-4-carboxaldehyde (12.26 g, 1.3 eq) was added dropwise therein at the temperature of −5° C.~−15° C. After completion of addition, the resulting mixture was incubated for 2 h. The resulting mixture was stirred at room temperature overnight, dried under reduced pressure to remove the DCM. 80 mL of ethanol and 5 mL of concentrated hydrochloric acid were added thereto. The resulting mixture was refluxed for 4 h, and then the reaction mixture was concentrated to a small volume and 100 mL of water was added. The resulting mixture was beaten and filtered to recover Compound II-1. The solid was washed with 20 mL of water. The aqueous phase was combined and extracted with methylene chloride/water, then drying the aqueous layer to give a tan oily substance which was purified by silica gel column chromatography to obtain 1.2 g of the solid compound V-3. Yield: 21.6%.

EI: 174 [M]+

EXAMPLE 10

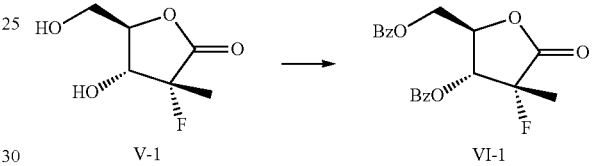

V-1           VI-1

Compound V-1 (2.56 g) was dissolved in 50 mL of ethyl acetate, and then adding triethylamine (8.75 mL, 4 eq) and 4-dimethylaminopyridine (DMAP) (0.75 g, 0.4 eq.). Benzoyl chloride (5.45 mL, 3eq) was slowly added dropwise at the temperature of −5° C.~5° C. The reaction completed two hours later indicating by TLC, the solid was filtered, and the filter cake was washed with 20 mL of ethyl acetate to give 3 g white flocculent solid Compound VI-1. HPLC purity was 97.5%. Yield: 51.2%.

$^1$HNMR(300 MHz, DMSO-d6) δ 1.68 (d,3H, J=24.2 Hz), 4.62-4.74 (m, 2H), 5.11-5.15 (m, 1H), 5.76 (dd, 1H, J=7.0, 18.4 Hz), 7.46 (m, 2H), 7.55 (m, 2H), 7.62 (m, 1H), 7.70 (m, 1H), 7.93 (m, 2H), 8.06 (m, 2H), 8.08 (m, 2H).

EXAMPLE 11

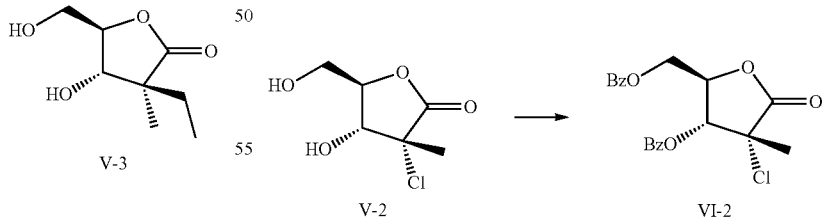

V-2           VI-2

Compound V-2 (2.78 g) was dissolved in 50 mL of ethyl acetate, and then adding triethylamine (8.6 mL, 4 eq) and DMAP (0.75 g, 0,44. Benzoyl chloride (5.45 mL, 3 eq) was slowly added dropwise at the temperature of −5° C.~5° C. The reaction completed two hours later indicating by TLC, the solid was filtered, and the filter cake was washed with 20 mL of ethyl acetate to give 2.9 g white flocculent solid Compound V1-2. HPLC purity was 98%. Yield: 50.5%.

$^1$HNMR(300 MHz, CDCl3) δ 1.93 (s,3H), 4.59 (dd, 1H), 4.80(dd, 1H), 4.96 (m, 1H), 5.63(d, 1H)7.40(t, 2H), 7.51 (t, 2H), 7.58 (t, 1H), 7.67 (t, 1H), 8.01 (m, 2H), 8.11 (m, 2H).

EXAMPLE 12

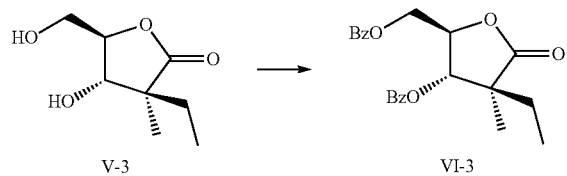

V-3    VI-3

Compound V-3 (2.72 g) was dissolved in 50 mL of ethyl acetate, and then adding triethylamine (8.6 mL, 4 eq) and DMAP (0.75 g, 0.4 eq). Benzoyl chloride (5.45 mL, 3 eq) was slowly added dropwise at the temperature of −5° C.~5° C. The reaction completed two hours later indicating by TLC, the solid was filtered, and the filter cake was washed with 20 mL of ethyl acetate to give 1.2 g white flocculent solid Compound V1-3. HPLC purity was 97.8%. Yield: 21.2%.

$^1$HNMR(300 MHz,CDCl3) δ (t, 3H), 1.37 (s, 3H), 1.80 (m, 2H), 4.58 (dd, 1H), 4.70-4.78 (m, 2H), 5.70 (d, 1H), 7.39 (t, 2H), 7.47 (t, 2H), 7.55 (t, 1H), 7.62 (t, 1H), 7.98-8.05 (m, 4H).

PREPARATION EXAMPLE 1

Preparation of 2-deoxy-2-fluoro-2-C-methyl-D-ribono-1,4-lactone mixture (Compound Aa)

Acetone-D-glyceraldehyde (39 g, 300 mmol) and ethyl 2-fluoropropionate (54 g, 450 mmol) were dissolved in dry tetrahydrofuran (150 mL), and then the mixture was added dropwise to a tetrahydrofuransolution (300 mL) containing lithium diisopropylamide (510 mmol) at the temperature of no more than −70° C. After the addition was complete, the temperature was gradually raised to room temperature. After stirring for 2 h, the reaction solution was poured into the saturated aqueous potassium dihydrogen phosphate solution (3000 mL). The organic solvent was evaporated by rotary evaporation. The residue was extracted with ethyl acetate, and concentrated to give an oily substance. Acetic acid (120 mL) and water (80 mL) were added to the concentrated oily substance. The resulting mixture was heated in oil bath at 90° C. for 2 h, and then removing acetic acid and water by rotary evaporation. The residue was dehydrated twice with anhydrous ethanol (20 mL×2).

Acetone (100 mL) was added to the residue, and then drying by evaporation again, so as to give an oily substance (70 g), i.e., 2-deoxy-2-fluoro-2-C-methyl-D-ribono-1,4-lactone mixture (Compound Aa).

EXAMPLE 13

Preparation of (2R)-2-deoxy-2-fluoro-2-C-methyl-D-ribono-1,4-lactone (Aa1)

Acetone (2 mL) was added to the oily substance (13.9 g) obtained in Preparation Example 1. The oily substance was completely dissolved by heating and stirring at 65° C., and methylene chloride (20 mL) was then added therein. The mixture was slowly cooled to room temperature. Subsequently, the mixture was placed into ice-water bath and stirred for 1.5 h, and the solid was gradually precipitated to give 2.6 g off-white solid by filtration. The mother liquor was preserved by evaporation under reduced pressure. The above-mentioned off-white solid was added to ethyl acetate (40 mL), and completely dissolved by heating. The resulting mixture was distilled to remove ethyl acetate, and the remainder was approximately 10 mL solution. The temperature of the remainder was slowly cooled to room temperature, and the solid was gradually precipitated to give 1.8 g off-white solid which is pure Compound Aa1.

$^1$HNMR(300 MHz, DMSO-d$_6$):δ 1.46 (d, 3H, J=24Hz), 3.55 (dd, 1H, J=12.8, 4.4 Hz), 3.73-3.80 (m, 1H), 3.96 (dd, 1H, J=24, 8 Hz), 4.20-4.28 (m, 1H).

EXAMPLE 14

Preparation of (2S)-2-deoxy-2-fluoro-2-C-methyl-D-ribono-1,4-lactone (Aa2)

Acetone (2.5 mL) was added to the preserved mother liquor in Example 13 and completely dissolved by heating and stirring at 50° C., then adding dichloromethane (10 mL). Subsequently, the resulting mixture was stirred for 1 h, and the solid was gradually precipitated and filtered, so as to obtain 1.4 g white solid (i.e. pure Compounds Aa2).

$^1$HNMR(300 MHz, DMSO-d$_6$): δ=1.48 (d, 3H, J=24 Hz), 3.40-3.70 (m, 1H), 3.75-3.95 (m, 1H), 4.05-4.15 (m, 1H), 4.30-4.50 (m, 1H).

EXAMPLE 15

Preparations of (2R)-2-deoxy-2-fluoro-2-C-me lactone (Aa1) and (2S)-2-deoxy-2-fluoro-2-C-methyl-D-ribono-1,4-lactone (Aa2)

Acetone (3 mL) was added to the oily substance (13.9 g) obtained in Preparation Example 1. The oily substance was completely dissolved by heating and stirring at 50° C., then adding methylene chloride (12 mL). The mixture was slowly cooled to room temperature. Subsequently, the mixture was placed into ice-water bath and stirred for 1.5 h, and the solid was gradually precipitated to give 1.62 g off-white solid by filtration which is pure Compound Aa1.

The mother liquor was preserved by evaporating, then adding acetone (2.5 mL). The preserved mother liquor was completely dissolved by heating and stirring at 60° C., and then adding methylene chloride (10 mL). The mixture was stirred for 1 h, and the solid was gradually precipitated and filtered, on as to give 1.4 g off-white solid, which is pure Compound Aa2.

EXAMPLE 16

Preparations of (2R)-2-deoxy-2-fluoro-2-C-methyl-D-ribono-1,4-lactone (Aa1) and (2S)-2-deoxy-2-fluoro-2-C-methyl-D-ribono-1,4-lactone (Aa2)

Ethyl acetate (20 mL) was added to the oily substance (13.9 g) Obtained in Preparation Example 1. The mixture was stirred for 30 minutes at room temperature, and gradually cooled to −5 °C. The solid was precipitated and filtered, so as to obtain 1.1 g Compound Aa1.

Subsequently, the mother liquor was dried by evaporation, and the same operation was carried out as in that in Example 14 to give 0.9 g Compound Aa2.

EXAMPLE 17

Preparations of (2R)-2-deoxy-2-fluoro-2-C-methyl-D-ribono-1,4-lactone (Aa1) and (2S)-2-deoxy-2-fluoro-2-C-methyl-D-ribono-1,4-lactone (Aa2)

Dichloromethane (20 mL) was added to the oily substance (13.9 g) obtained in Preparation Example 1. The mixture was stirred for 30 minutes at room temperature to precipitate the solid gradually. The solid was filtered to obtain a mixture of Compounds Aa1 and Aa2, and the mother liquor was preserved. The mixture was dissolved in acetone (7 mL) by heating to 70° C., and was slowly cooled to −10° C. The solid was precipitated and filtered, so as to obtain 1.2 g pure Compound Aa1.

Subsequently, the preserved mother liquor was cooled to 0° C., then adding dichloromethane (10 mL). The resulting mixture was stirred overnight to precipitate the solid, so as to obtain 1 g of the mixture of Compounds Aa1 and Aa2. The mixture was dissolved in acetone (1.5 mL) by heating, and slowly cooled to −10° C. to preipitate the solid. The mixture was filtered to give 0.6 g pure Compound Aa2.

EXAMPLE 18

Preparations of (2R)-2-deoxy-2-fluoro-2-C-methyl-D-ribono-1,4-lactone (Aa1) and (2S)-2-deoxy-2-fluoro-2-C-methyl-D-ribono-1,4-lactone (Aa2)

Dichloromethane (20 mL) was added to the oily substance (13.9 g) obtained in Preparation Example 1. The mixture was stirred for 30 minutes at room temperature to precipitate the solid gradually. The solid was filtered to obtain a mixture of Compounds Aa1 and Aa2, and the mother liquor was preserved. The mixture was dissolved in tetrahydrofuran (14 mL) by heating to 60° C., and the toluene (3 mL was added therein. The resulting mixture was slowly cooled to room temperature to precipitate the solid. The mixture was filtered to give 1.1 g pure Compound Aa1.

The processing method for the mother liquor is the same as that in Example 14, which can obtain 0.65 g pure Compound Aa2.

EXAMPLE 19

Preparations of (2R)-2-deoxy-2-fluoro-2-C-methyl-D-ribono-1,4-lactone (Aa1) and (2S)-2-deoxy-2-fluoro-2-C-methyl-D-ribono-1,4-lactone (Aa2)

Dichloromethane (20 mL) was added to the oily substance (13.9 g) obtained in Preparation Example 1. The mixture was stirred for 30 minutes at room temperature to precipitate the solid gradually. The mixture of Compounds Aa1 and Aa2 was obtained by filtration, and the mother liquor was preserved. The mixture was dissolved in tetrahydrofuran (10 mL) by heating to 80° C., and was slowly cooled to room temperature to precipitate the solid. The mixture was filtered to give 1.2 g pure Compound Aa1.

The processing method for the mother liquor is the same as that in Example 14, so 0.6 g pure Compound Aa2 was obtained.

EXAMPLE 20

Preparation of (2R)-3,5-dibenzoyl-2-fluoro-2-C-methyl-D-ribono-1,4-lactone

Compound Aa1 (1.48 g) was dissolved in acetone (15 mL), and then adding triethylamine (3.1 mL) and DMAP (100 mg). The mixture was cooled in ice-water bath for 5 minutes. Subsequently, benzoic anhydride (4.5 g) was added thereto, and the resulting mixture was stirred overnight. The above-mentioned reaction solution was added to 100 mL of ethyl acetate. The resulting mixture was washed twice with 30 mL water, twice with 30 mL, dilute hydrochloric acid and once with saturated aqueous sodium chloride solution, and then dried over anhydrous sodium sulfate and filtered to obtain the filtrate. The filtrate was dried by evaporation to give an oily substance. 30 mL of isopropanol was added to the oily substance, and the resulting mixture was stirred for 40 minutes to precipitate the solid gradually. The mixture was filtered to give 3 g of the title compound. HPLC purity is greater than 99%.

$^1$HNMR(300 MHz, DMSO-d$_6$) δ 1.68 (d,3H, J=24.2 Hz), 4.62-4.74 (m, 2H), 5.11-5.15 (m, 1H), 5.76 (dd, 1H, J=7.0, 18.4 Hz), 7.46 (m, 2H), 7.55 (m, 2H), 7.62 (m, 1H), 7.70 (m, 1H), 7.93 (m, 2H), 8.06 (m, 2H), 8.08 (m, 2H).

The above examples are only for illustrative purpose, the scope of the present invention is not limited thereto. It is apparent for a person skilled in the art to make modifications or variations, and the present invention is limited only by the scope of the appended claims.

What is claimed is:

1. A method for synthesizing (2R)-2-deoxy-2,2-disubstituted-ribono-1,4-lactone represented by General Formula V, which is carried out by the following reaction Formula:

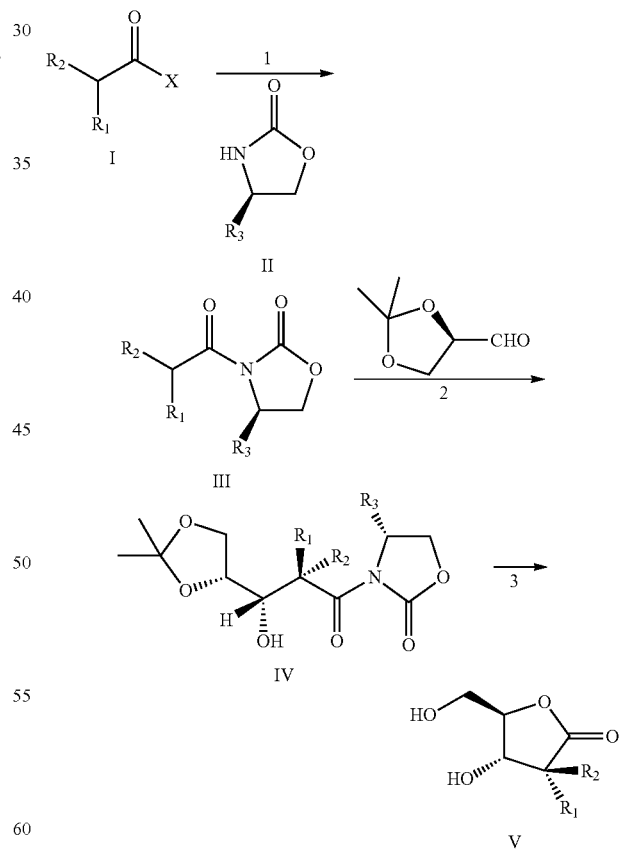

wherein $R_1$ and $R_2$ are different and are each independently selected from the group consisting of hydrogen, halogen, nitrile group, carbamoyl group and $C_1$-$C_3$ linear or branched alkyl group; $R_3$ is phenyl or t-butyl; and X is hydroxyl or halogen, the method comprises the steps of:
1) performing a condensation reaction between the compound represented by Formula I and the compound represented by the Formula II in the presence of a condensing agent to obtain a compound represented by Formula III, in the case that X is hydroxyl, or performing an acylation reaction between the compound represented by Formula I and the compound represented by the Formula II in the presence of an acid binding agent to obtain the compound represented by Formula III, in the case that X is halogen;
2) performing an Aldol condensation reaction between the compound represented by Formula III and (R)-(+)-2,2-dimethyl-1,3-dioxolane-4-carboxaldelyde in the presence of a Lewis acid and an organic base to obtain a compound represented by Formula IV, wherein the Lewis acid is titanium tetrachloride; and
3) performing a deprotection reaction and ring closure of the compound represented by Formula IV in an acidic system to obtain a compound represented by General Formula V, wherein the acidic system is a mixture of hydrocloric acid, sulfuric acid, acetic acid or trifluoroacetic acid and alcoholic solvent.

2. The method according to claim 1, wherein the condensing agent used in Step 1) is selected from the group consisting of dicyclohexyl carbodiimide and 1-ethyl-(3-dimethylaminopropyl)carbodiimide; the acid binding agent used in Step 1) is selected from the group consisting of potassium carbonate, sodium carbonate, triethylamine, pyridine, N,N-dimethyl-4-aminopyridine, diisopropylethylamine and imidazole; the solvent used in Step 1) is selected from the group consisting of dichloromethane, 1,2-dichloroethane, tetrahydrofuran, 1,4-dioxane, toluene, acetonitrile, ethyl acetate and ethylene glycol dimethyl ether.

3. The method according to claim 1, wherein the organic base used in Step 2) is selected from the group consisting of triethylamine, diisopropylethylamine, 1,8-diazabicyclo[5.4.0]undec-7-ene, pyridine and N,N-dimethyl-4-aminopyridine; the solventused in Step 2) is selected from the group consisting of dichloromethane, 1,2-dichloroethane, tetrahydrofuran, 1,4-dioxane, toluene, acetonitrile, ethyl acetate and ethylene glycol dimethyl ether.

4. The method according to claim 1, wherein the alcoholic solvent in the acidic system in Step 3) is methanol, ethanol, propanol or isopropanol.

* * * * *